Figure 1:
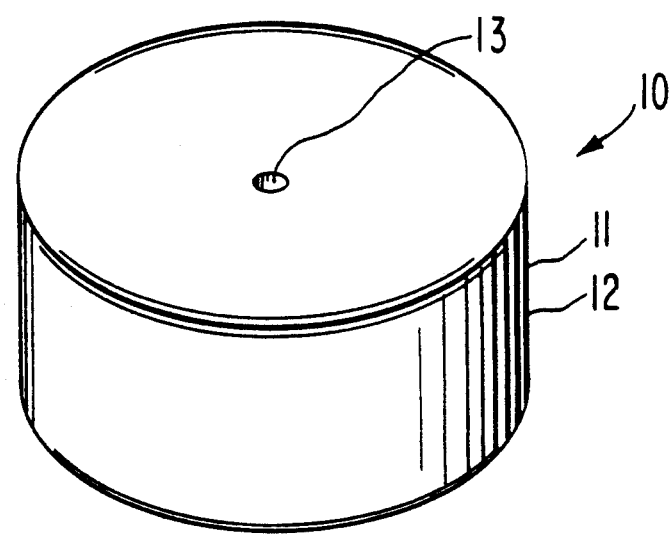

United States Patent [19]
Edgren et al.

[11] Patent Number: 5,221,536
[45] Date of Patent: Jun. 22, 1993

[54] DOSAGE FORM INDICATED FOR THE MANAGEMENT OF ABNORMAL POSTURE, TREMOR AND INVOLUNTARY MOVEMENT

[75] Inventors: David E. Edgren, El Granada; Howard A. Carpenter, Palo Alto; Gurdish K. Bhatti, Fremont; Atul D. Ayer, Palo Alto, all of Calif.

[73] Assignee: ALZA Corporation, Palo Alto, Calif.

[21] Appl. No.: 717,293

[22] Filed: Jun. 17, 1991

Related U.S. Application Data

[63] Continuation of Ser. No. 520,295, May 7, 1990, Pat. No. 5,190,763.

[51] Int. Cl.⁵ ............................................. H61K 9/24
[52] U.S. Cl. .................................... 424/473; 424/472
[58] Field of Search ...................... 424/473, 472, 468

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,014,334 | 3/1977 | Theeuwes et al. | 128/260 |
| 4,058,122 | 11/1977 | Theeuwes et al. | 128/260 |
| 4,077,407 | 3/1978 | Theuwess et al. | 128/260 |
| 4,111,202 | 9/1978 | Theeuwes | 128/260 |
| 4,116,241 | 9/1978 | Theeuwes et al. | 128/260 |
| 4,160,020 | 7/1979 | Ayer et al. | 424/15 |
| 4,235,236 | 11/1980 | Theeuwes | 128/260 |
| 4,256,108 | 3/1981 | Theeuwes | 128/260 |
| 4,519,801 | 5/1985 | Edgren | 604/892 |
| 4,522,625 | 6/1985 | Edgren | 604/892 |
| 4,576,604 | 3/1986 | Guittard et al. | 604/890 |
| 4,743,247 | 5/1988 | Wong | 424/468 |

Primary Examiner—Thurman K. Page
Assistant Examiner—Leon R. Horne
Attorney, Agent, or Firm—Paul L. Sabatine; Robert Scott Meece; Edward L. Mandell

[57] ABSTRACT

A dosage form is disclosed comprising an anti-Parkinson's disease drug for administering to a patient in need of anti-Parkinson's disease therapy.

7 Claims, 2 Drawing Sheets

U.S. Patent     June 22, 1993     Sheet 1 of 2     5,221,536

5,221,536

DOSAGE FORM INDICATED FOR THE MANAGEMENT OF ABNORMAL POSTURE, TREMOR AND INVOLUNTARY MOVEMENT

CROSS-REFERENCE TO RELATED APPLICATIONS

This application is a continuation of U.S. Ser. No. 07/520,295 filed on May 7, 1990, U.S. Pat. No. 5190763 which application is incorporated herein by reference, and benefit is claimed of its filing date. This application is assigned to the ALZA Corporation of Palo Alto, Calif.

DESCRIPTION OF TECHNICAL FIELD

This invention pertains to a dosage form comprising at least one drug indicated for the management of abnormal posture, tremor and involuntary movement. More particularly, the invention concerns a dosage form that administers at least one therapeutically useful drug for treating Parkinson's disease.

DESCRIPTION OF BACKGROUND ART

In 1817, James Parkinson described Parkinson's disease as paralysis agitans. The most common symptoms for paralysis agitans are constant tremors in the hands and legs, body movements that become stiff, slow and weak with near paralysis, and sober-mask like facial expressions. Patients suffering with this disease have difficulty in maintaining an erect posture as they often have a stooped appearance, and they lean forward while walking with a shuffling gait.

The pathological cause of Parkinson's disease involves destruction of the nerve cells in the substantia nigra part of the brain, the part of the brain involved with muscle movements. The nerve cells of the substantia nigra use an in vivo chemical dopamine for transmitting signals between each other, and it is the absence of dopamine that leads to Parkinson's symptoms. Consequently, present medical treatment for Parkinson's disease comprises administering a drug that acts on the basal ganglia to exert a dopaminergic or an anticholinergic effect, or administering a drug that substantially lessens or blocks the body's monamine oxidase from metabolizing nerve cell dopamine. The medical history of Parkinson's disease is presented in *The Pharmacological Basis of Therapeutics,* by Goodman and Gilman, 7th Ed., Chap. 21, (1985), published by Macmillan Publishing Company, New York. The drugs administered by the prior art for treating Parkinson's disease are administered usually from a tablet or a capsule. These forms deliver a drug in a bulk, non-rate uncontrolled dumping dose that is subject also to the changing adverse environment of the gastrointestinal tract.

In the light of the above presentation, it will be appreciated by those versed in the drug dispensing art to which this invention pertains, that a pressing need exists for a dosage form that can administer a drug for treating Parkinson's disease at a controlled rate in a constant dose per unit time over a prolonged period of time. The need exists for an oral dosage form that can administer an anti-Parkinson's disease drug for its therapeutic dopaminergic, anti-cholinergic, or anti-monoamine oxidase effect substantially independent of the variable environment of the gastrointestinal effect. It will be appreciated further by those versed in the dispensing art, that such a novel and unique dosage form that can administer an anti-Parkinson's disease drug in a rate controlled dose over time, and simultaneously provide therapy in the brain, would represent an advancement and a valuable contribution to the art.

DISCLOSURE OF OBJECTS OF THE INVENTION

Accordingly, in view of the above presentation, it is an immediate object of this invention to provide a novel dosage form for delivering a drug for treating Parkinson's disease, and which dosage form substantially overcomes the deficiencies associated with the prior art.

Another object of the present invention is to provide a dosage form for administering at least one drug over a prolonged period of time for treating Parkinson's disease.

Another object of the present invention is to provide a pharmaceutically acceptable composition comprising a drug for treating Parkinson's disease, and which pharmaceutically acceptable composition can be delivered from a dosage form manufactured as a drug delivery device.

Another object of the present invention is to provide a pharmaceutically acceptable composition comprising a drug pair indicated for treating Parkinson's disease, and which pharmaceutically acceptable composition can be delivered from a dosage form manufactured as a drug delivery device.

Another object of the present invention is to provide a novel dosage form manufactured as an osmotic device that can administer an anti-Parkinson drug to a human receptor in need of anti-Parkinson therapy.

Another object of the present invention is to provide a novel and unique dosage form manufactured as an osmotic dosage form that can deliver an anti-Parkinson drug and concurrently substantially reduce and/or substantially eliminate the unwanted influences of the gastrointestinal environment of use and still provide controlled administration of the anti-Parkinson drug over time.

Another object of the present invention is to provide a dosage form adapted for oral administration of an anti-Parkinson drug, which dosage form comprises a first composition comprising an anti-Parkinson drug, and a second composition for the rate-controlled administration of the first composition comprising the anti-Parkinson drug.

Another object of the present invention is to provide a complete pharmaceutical regimen for the management of Parkinson's disease, which regimen comprises a composition comprising an anti-Parkinson drug that can be dispensed from a drug delivery device, the use of which requires intervention only for initiation and possibly for termination of the regimen.

Another object of the presented invention is to provide a carrier composition for an anti-Parkinson drug, wherein the ingredients forming the carrier composition and the anti-Parkinson drug are in close contact substantially-free of interaction.

Another object of the present invention is to provide a composition for delivering an anti-Parkinson drug, wherein the ingredients forming the composition are free from exerting an adverse or deteriorating effect of the anti-Parkinson drug.

Another object of the present invention is to provide a dosage form designed and manufactured as an osmotic device containing an anti-Parkinson drug that is delivered in a dose amount for producing the desired therapeutic effect, and which device delivers substantially a full complement of the drug thereby avoiding the need for drug overage for delivering the needed dose.

Another object of the invention is to provide a method for treating Parkinson's disease by orally administering an anti-Parkinson drug in a rate controlled dose per unit time to a warm-blooded animal in need of anti-Parkinson therapy.

Other objects, features and advantages of the invention will be more apparent to those versed in the dispensing arts from the following detailed specification, taken in conjunction with the drawings, and the accompanying claims.

BRIEF DISCLOSURE OF THE DRAWING

Figure 2:
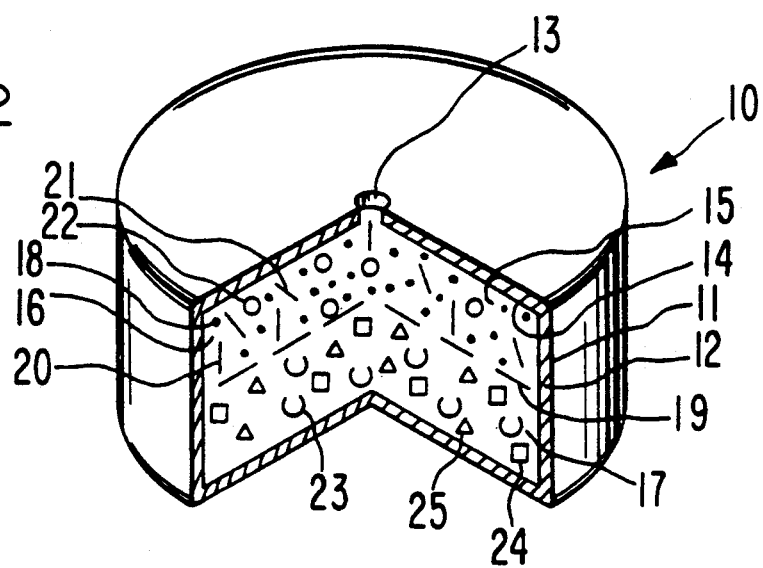
Figure 3:
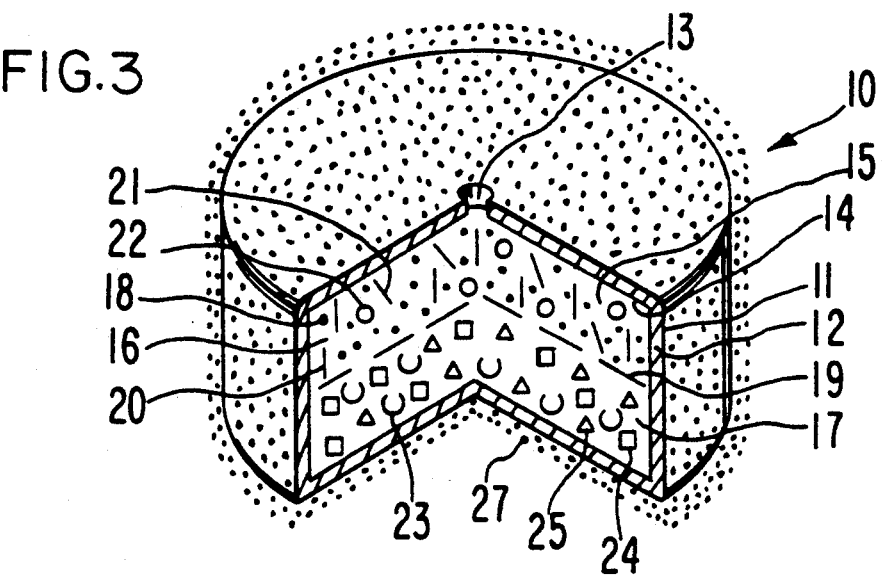
Figure 4:
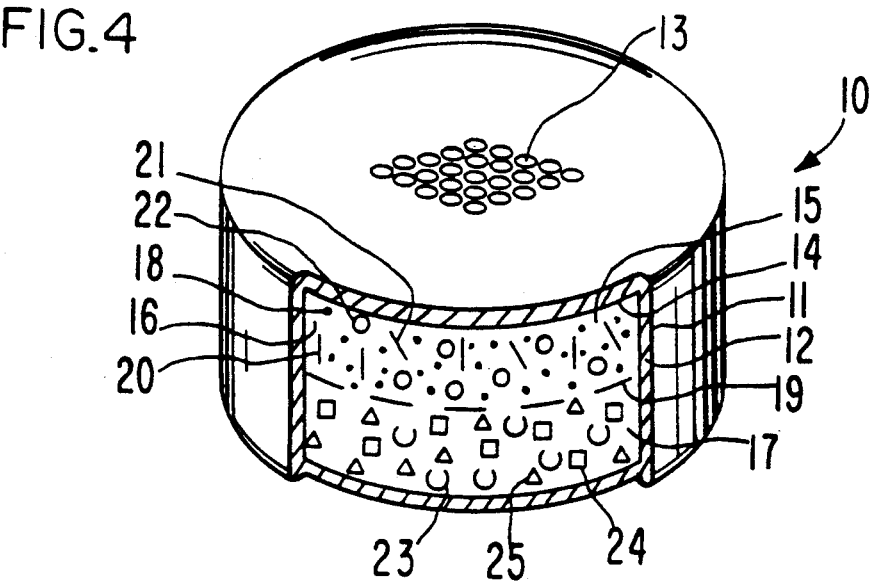
Figure 5:
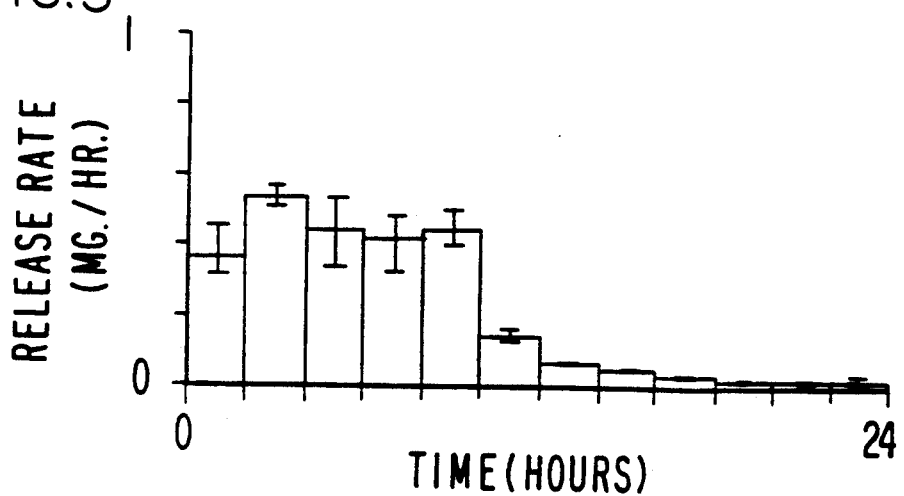
Figure 6:
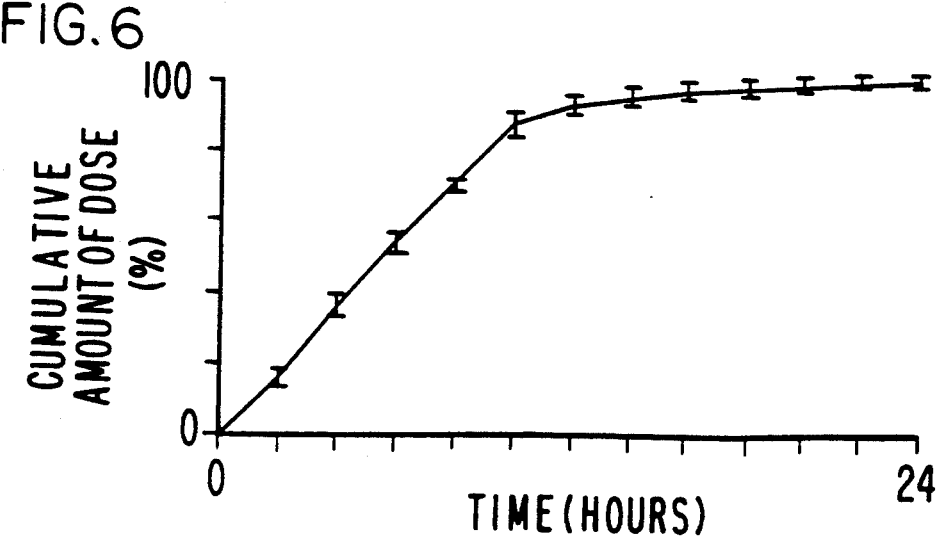

In the drawing figures, which are not drawn to scale, but are set forth to illustrate various embodiments of the invention, the drawing figures are as follows:

Drawing FIG. 1 is a view of a dosage form designed, shaped and adapted for orally administering an anti-Parkinson drug to the gastrointestinal tract of a human in need of anti-Parkinson therapy:

Drawing FIG. 2 is an opened view of the dosage form of drawing FIG. 1 for illustrating the internal structure of the dosage form;

Drawing FIG. 3 is an opened view of the dosage form of drawing FIG. 1, wherein drawing FIG. 3 comprises a microporous inlay for releasing an anti-Parkinson drug from the dosage form;

Drawing FIG. 4 is an opened view of the dosage form of drawing FIG. 1, wherein drawing FIG. 4 further depicts an external, instant-release anti-Parkinson drug coated on the exterior surface of the dosage form:

Drawing FIG. 5 is a graph that depicts the dose amount of an anti-Parkinson drug released per hour over a prolonged period of 24 hours from a dosage form provided by the invention; and, Drawing FIG. 6 is a graph depicting the cumulative amount of an anti-Parkinson drug delivered by a dosage form over a prolonged period of time up to 24 hours.

In the drawing figures and in the specification, like parts in related drawing figures are identified by like numbers. The terms appearing earlier in the specification and in the description of the drawing figures, as well as embodiments thereof, are further described elsewhere in the specification.

DETAILED DISCLOSURE OF THE DRAWING FIGURES

Turning now to the drawing figures in detail, which drawing figures are an example of the dosage form provided by-this invention, and which example is not to be construed as limiting, one example of the dosage form is illustrated in drawing FIG. 1 and designated by the numeral 10. In drawing FIG. 1, dosage form 10 comprises a body member 11 comprising wall 12 that surrounds an enclosed internal compartment, not seen in drawing FIG. 1. Dosage form 10 comprises at least one exit means 13 in wall 12, which exit means 13 connects the exterior environment of use with the interior of dosage form 10.

In drawing FIG. 2, dosage form 10 is manufactured as an osmotic device, and it is seen in opened view. In drawing FIG. 2, dosage form 10 comprises body 11, wall 12, that is sectioned at 14, and which wall 12 surrounds and defines an internal compartment 15. Wall 12 comprises at least one exit means 13 that connects compartment 15 with the exterior of dosage form 10. Dosage form 10 can comprise more than one exit means 13, as presented later in the specification.

Wall 12 of dosage form 10, comprises totally, or in at least a part, a composition that is permeable to the passage of an exterior fluid present in the environment of use. Wall 12 is substantially impermeable to the passage of a therapeutic anti-Parkinson's disease drug and other optional ingredients that may be present in compartment 15. The semipermeable wall 12 is substantially inert, that is, it maintains its physical and chemical integrity during the dispensing of a therapeutically active anti-Parkinson's disease drug from dosage form 10. Wall 12 in a presently preferred embodiment is formed totally or in at least a part of a member selected from the group consisting of a cellulose ether, cellulose ester, cellulose ester-ether. The cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%: cellulose acetate having an acetyl content of 32 to 39.8%: cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8 an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional semipermeable polymers include acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable crosslinked selectively permeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked ply(vinylbenzyltrimethyl ammonium chloride). The polymers are known to the art in U.S. Pat. Nos. 3,845,770; 3,916,899; and 4,160,020; and in *Handbook of Common Polymers* by Scott, J. R. and Roff, W. J., 1971, published by CRC Press, Cleveland, Ohio.

In another embodiment, wall 12 comprises additionally from 0 weight percent (wt %) to 30 wt % of a member selected from the group consisting of a cellulose ether selected from the group consisting of a hydroxypropylcellulose and a hydroxypropylmethylcellulose, and from 0 wt % to 30 wt % of a polyethylene glycol. The total weight of all components comprising wall 12 is equal to 100 wt %.

Internal compartment 15 comprises a first composition 16, which first composition 16 also can be defined as a first lamina 16. The internal compartment 15 comprises a second composition 17 which also can be defined as a second composition 17. The first composition 16 and the second composition 17 initially are in laminar arrangement and they cooperate with each other and with dosage form 10 for effectively delivering an anti-Parkinson's disease drug from dosage form 10.

First composition 16 comprises an anti-Parkinson's disease drug 18, represented by dots, which anti-Parkinson's disease drug comprises at least one member selected from the group consisting of bromocriptine; bromocriptine and its therapeutically acceptable salts; bromocriptine mesylate; ergot derivatives including lisuride, pergolide, and mesulergine; levodopa; carbidopa; levodopa/carbidopa; amantadine; eldepryl (also known as selegilene); trihexyphenidyl; benztropine; biperiden; ethopropazine; procyclidine; dopamine agonist, monamine oxidase inhibitors, anticholinergic including benztropine mesylate, trihexyphenidyl hydrochloride, procyclidine hydrochloride, biperiden hydrochloride, and ethopropazine hydrochloride; and the like.

The dose amount of an anti-Parkinson's disease drug 18 in the first composition for drug 18 comprises 1 mg to 10 mg for benztropine; 2 mg to 15 mg of biperiden; 15 mg to 175 mg of diphenhydramine; 75 mg to 750 mg of ethopropazine: 2 mg to 50 mg of procyclidine: 1 mg to 30 mg of trihexyphenidyl; 50 mg to 450 mg of amantadine; 50 mg to 500 mg of carbidopa/levodopa; 1 mg to 50 mg of bromocriptine; 0.10 mg to 25 mg of pergolide; 1 mg to 50 mg of eldepryl; 50 mg to 600 mg of levodopa; anti-Parkinson drug pairs comprising 2 mg to 20 mg trihexyphenidyl and 1 mg to 30 mg bromocriptine: 1 mg to 30 mg bromocriptine and 200 mg to 600 mg levodopa; 15 mg to 100 mg carbidopa and 1 mg to 30 mg bromocriptine and 1 mg to 50 mg eldepryl: 1 mg to 50 mg eldepryl and 200 mg to 600 mg levodopa; 1 mg to 50 mg eldepryl and 50 mg to 450 mg amantadine: 1 mg to 50 mg eldepryl and 50 mg to 500 mg carbidopa/levodopa; and the like. Generally the first composition 16 comprises from 1 mg to 600 mg of at least one, of more than one such as a pair of anti-Parkinson's disease drug comprising from 1 mg to 750 mg.

The first composition 16 also comprises from 0 wt % to 35 wt % of a hydroxypropylmethlcellulose, identified by dashes 19 comprising a 9,000 to 125,000 average molecular weight; from 0 wt % to 75 wt % of a hydroxypropylcellulose represented by vertical lines 20 comprising a 10,000 to 300,000 molecular weight; from 0 wt % to 75 wt % of a polyvinyl pyrrolidone represented by slanted lines 21 and comprising a 20,000 to 275,000 molecular weight; and optionally from 0 wt % to 10 wt % of an acid represented by circles 22 comprising inorganic and organic acids exemplified by a member selected from the group consisting of malic, fumaric, tartaric, itaconic, maleic, citric, adipic, succinic and itaconic; with the total weight percent of all ingredients in the first composition equal to 100 wt %. The first composition 16 optionally comprises from 0 wt % to 3 wt % of a tabletting excipient, for example, a lubricant, such as magnesium stearate, a flow-promoting agent such as colloidal silicon dioxide, and the like, and optionally 0 wt % to 3 wt % surfactant.

Second composition 17 comprises from 0 wt % to 45 wt % of an osmotically effective compound, which compounds are know also as osmotically effective solutes and osmagents, and they are represented in drawing FIG. 2 by half-circles 23. The osmotic solutes 23 are homogeneously or heterogeneously mixed with other composition 17 forming ingredients for imbibing an external fluid through wall 12 into composition 17. Osmotically effective solutes used for the purpose of this invention comprise magnesium sulfate, magnesium chloride, potassium sulfate, sodium sulfate, lithium sulfate, d-mannitol, area, inositol, magnesium succinate, sodium chloride, potassium chloride, raffinose, sucrose, glucose, lactose, and the like. Osmotic solutes and procedures for measuring the osmotic pressure using a Model 320B, Vapor Pressure Osmometer, manufactured by the Hewlett Packard Co., Avondale, Pa., are disclosed Wong et al in U.S. Pat. No. 4,765,989.

Second composition 17 comprises also from 35 wt % to 85 wt % of an osmopolymer 24, identified by squares. Osmopolymer 24 imbibes an aqueous fluid, such as a biological fluid or water through wall 12 into the osmopolymer, and it retains a significant volume of the fluid causing it to expand from 2 to 60 fold. The expansion of osmopolymer 24 against first composition 16 causes the delivery of the anti-Parkinson drug through exit means 13. The osmopolymer 24 present in second composition 17 for the purpose of this invention comprise a cellulose ether such as an alkali cellulose ether, sodium carboxymethylcellulose, potassium carboxymethylcellulose, lithium carboxymethylcellulose, sodium cellulose glycollate and glycolcellulose; and a blend of an alkali cellulose ether with at least one of a hydroxypropylcellulose or a hydroxypropylmethylcellulose, identified by triangles 25, and wherein the amount of hydroxypropylcellulose or hydroxypropylmethylcellulose is from 5 wt % to 35 wt %. Second composition 17 optionally comprises from 0 wt % to 3 wt % of a coloring agent such as ferric oxide, optionally from 0 wt % to 3 wt % of flow-promoting agent such as silicon dioxide, and optionally from 0 wt % to 3 wt % of a lubricant such as stearic acid: with the weight percent of all ingredients present in second composition 17 equal to 100 wt %.

Dosage form 10, as seen in opened section in drawing FIG. 3, depicts an optional embodiment of the invention, that comprises an external coat 26 on the exterior surface of wall 12. Coat 26 is a composition comprising 1 mg to 100 mg of an anti-Parkinson drug 27, represented by dots, and an aqueous soluble film-forming carrier such as methylcellulose, hydroxypropylcellulose, hydroxypropylmethylcellulose, blends of hydroxypropylcellulose and hydroxypropylmethylcellulose, optionally blended with a plasticizer such as polyethylene glycol or acetylated triglycerides or the like. Coat 26 provides instant anti-Parkinson therapy, as film coat 26 dissolves or undergoes dissolution in the presence of fluid and concurrently therewith delivers anti-Parkinson drug 27 to drug receptor. Coat 26 comprising anti-Parkinson 27, by providing immediate anti-Parkinson drug delivery, essentially overcomes the time required for anti-Parkinson drug 18 to be delivered from compartment 15. A start-up time is needed for imbibing fluid through wall 12 for device 10 to hydrodynamically dispense anti-Parkinson drug 17 through exit means 13.

Drawing FIG. 4 depicts, in opened section, another anti-Parkinson drug delivery device provided by the invention. In drawing FIG. 4, exit means 13 comprises a microporous inlay that spreads the drug as it is osmotically released from the dosage form 10. The expression, "exit means" 13, as used herein, comprises means and methods suitable for the metered release of a beneficial anti-Parkinson drug from compartment 15 of dosage form 10. The means 13 includes at least one passageway, orifice, or the like, through wall for communicating with the anti-Parkinson drug in compartment 15. The expression "at least one passageway", includes aperture, orifice, bore, pore, porous element through which the drug can be pumped, diffuse, travel or migrate, hollow fiber, capillary tube, porous overlay, porous insert, microporous member, and the like. The expression also includes a material that erodes or is leached from wall 12 in the fluid environment of use to produce at lease one passageway in dosage form 10. Representative material suitable for forming at least one passageway, or a multiplicity of passageways, include an erodible poly(-glycolic) acid or poly(lactic) acid member in the wall; a gelatinous filament: poly(vinyl alcohol); leachable materials such as fluid removable pore forming polysaccharides, salts, or oxides, and the like. A passageway or a plurality of passageways can be formed by leaching a material such as sorbitol, sucrose, lactose, fructose or the like, from the wall. The passageway can have any shape such as round, triangular, square, elliptical, and the like, for assisting in the metered release of drug from dosage form 10. Dosage form 10 can be constructed with one or more passageways in spaced apart relation on one or more than a single surface of a dosage form. Passageways and equipment for forming passages are disclosed in U.S. Pat. Nos. 3,845,770 and 3,916,899 by Theeuwes and Higuchi; in U.S. Pat. No. 4,063,064 by Saunders et al; and in U.S. Pat. No. 4,088,864 by Theeuwes et al. Passageways formed by teaching to provide a drug-releasing pore of controlled osmotic release rate are disclosed in U.S. Pat. No. 4,200,098 by Ayer et al; and in U.S. Pat. No. 4,285,987 by Ayer et al.

Dosage form 10 of this invention, and as seen in the above drawing figures, can be manufactured for administering an anti-Parkinson's disease drug by the oral route, and in another embodiment the dosage form can be sized and shaped for administering an anti-Parkinson's disease drug by the sublingual and buccal routes. The sublingual and buccal routes can be used for quicker therapy and they can be used when a smaller dose of drug is needed for therapy. The latter routes can be used as a by-pass of the first pass of hepatic metabolism of the anti-Parkinson's disease drug. The sublingual or buccal routes can be used for administering a drug such as eldepryl, levodopa-carbidopa and the like, and for administering more than one drug such as eldepryl as an adjunct in the management of Parkinsonian patients being treated with levodopa-carbidopa, and the like.

Wall 12 of osmotic dosage form 10 can be formed in one technique using the air suspension procedure. This procedure consists in suspending and tumbling the compressed laminate in a current of air and wall forming composition until a wall is applied to the drug forming compartment. The air suspension procedure is well-suited for independently forming the wall. The air suspension procedure is described in U.S. Pat. No. 2,799,241; J. Am. Pharm. Assoc., Vol. 48, pp 451 to 459, 1959; and ibid, Vol. 49, pp 82 to 84, 1960. Osmotic dosage forms can also be coated with a wall-forming composition in a Wurster ® air suspension coater, using methylene dichloride-methanol cosolvent, 80:20, wt:wt, or acetone-water cosolvent, 90:10, wt:wt using 2.5 to 4% solids. The Aeromatic ® air suspension coater using a methylene dichloride-methanol cosolvent, 87:13, wt:wt, also can be used for applying the wall. Other wall forming techniques such as pan coating can be used for providing the dosage form. In the pan coating system, wall forming compositions are deposited by successive spraying of the composition on the bilayered compartment, accompanying by tumbling in a rotating pan. A pan coater is used to produce thicker walls. A larger volume of methanol can be used in a cosolvent to produce a thinner wall. Finally, the wall coated compartments are dried in a forced air oven at 30° C. to 50° C. for up to a week to free the dosage form of solvent. Generally, the walls formed by these techniques have a thickness of 2 to 20 mils with a presently preferred thickness of 4 to 10 mils.

Dosage form 10 of the invention is manufactured by standard manufacturing techniques. For example, in one manufacture the beneficial drug and other ingredients comprising the first layer facing the exit means are blended and pressed into a solid layer. The drug and other ingredients can be blended also with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer, or hydrogel layer, is placed in contact with the drug layer. The layering of the drug layer and the osmopolymer layer can be fabricated by conventional press-layering techniques. Finally, the two-layer compartment forming members are surrounded and coated with an outer wall. A passageway is laser drilled through the wall to contact the drug layer, with the dosage form optically oriented automatically by the laser equipment for forming the passageway on the preselected surface.

In another manufacture, the dosage form is manufactured by the wet granulation technique. In the wet granulation technique, the drug and the ingredients comprising the first layer are blended using an organic solvent, such as isopropyl alcohol-methylene dichloride 80/20 v/v (volume/volume) as the granulation fluid. Other granulating fluid such as denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through an 80 mesh screen and added to the dry screen granule blend. The granulation is put into milling jars and mixed on a jar mill for 1 to 15 minutes. The composition is pressed into layers, for example in a Manesty ® press layer press. The second layer is pressed in a similar manner.

Another manufacturing process that can be used for providing the compartment-forming composition comprises blending the powdered ingredients in a fluid bed granulator. After the powdered ingredients are dry blended in the granulator, a granulating fluid, for example poly(vinyl-pyrrolidone) in water, or in denatured alcohol, or in 95/5 ethyl alcohol/water, or in blends of ethanol and water is sprayed onto the powders. Optionally, the drug can be dissolved or suspended in the granulating fluid. The coated powders are then dried in a granulator. This process granulates all the ingredients present therein while adding the granulating fluid. After the granules are dried, a lubricant such as stearic acid or magnesium stearate is added to the granulator. The granules are pressed then in the manner described above.

The osmotic device of the invention is manufactured in another embodiment by mixing an anti-Parkinson drug with composition forming ingredients and pressing the composition into a solid lamina possessing dimensions that correspond to the internal dimensions of the compartment space adjacent to a passageways. In another embodiment the drug and other first composition forming ingredients and a solvent are mixed into a solid, or a semisolid, by conventional methods such a ballmilling, calendering, stirring or rollmilling, and then pressed into a preselected lamina forming shape. Next, a lamina of a composition comprising an osmopolymer and an optional osmagent are place in contact with the lamina comprising the drug, and the two lamina comprising the laminate are surrounded with a semipermeable wall. The lamination of the first drug composition and the second osmopolymer optional osmagent composition can be accomplished by using a conventional two-layer tablet press technique. The wall can be applied by molding, spraying or dipping the pressed shapes into wall forming materials. Another and presently preferred technique that can be used for applying the wall is the air suspension coating procedure. This procedure consists in suspending and tumbling the two layered laminate in current of air until the wall forming composition surrounds the laminate. The air suspension procedure is described in U.S. Pat. No. 2,799,241; *J. Am. Pharm. Assoc.*, Vol. 48, pp 451–459 (1979); and, ibid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1979, (1970), published by Mack Publishing Co., Easton, Pa.

Exemplary solvents suitable for manufacturing the wall, the laminates and laminae include inert inorganic and organic solvents that do not adversely harm the materials and the final wall of the final laminated wall. The solvents broadly include members selected for the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane ethylene glycol monoethyl ether, ethylene glycol monoethyl acetate, methylene dichloride, ethylene dichloride, propylene dichloride, carbon tetrachloride, chloroform, nitroethane, nitropropane, tetrachoroethan, ethyl ether, isoproyl ether, cyclohexane, cyclo-octane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to these versed in the art in the light of the present disclosure, the drawings and accompanying claims.

EXAMPLE 1

A dosage form adapted, designed and shaped as an osmotic drug delivery is manufactured as follows: first, the anti-Parkinson drug containing composition is prepared by adding 1700 ml of anhydrous ethyl alcohol to stainless steel vessel and its mixer started for stirring the alcohol. Then, 150 g of polyvinyl pyrrolidone having a 40,000 molecular weight is added to the anhydrous ethyl alcohol with continuous mixing to produce a solution. Then, 50 g of bromocriptine mesylate is added to the polyvinyl pyrrolidone solution and the mixing continued until all the ingredients are well-dispersed in the solvent.

Next, blend 608.3 g of hydroxypropylcellulose having a 60,000 molecular weight, 31.7 g of maleic acid and 150 g of polyvinyl pyrrolidone to provide a homogeneous composition that is screened through a 40 mesh screen. The freshly screened composition next is added to a granulator column preheated to 40° C. Then, the solution comprising the bromocriptine and the polyvinyl pyrrolidone is sprayed onto the column at a rate of 40–55 ml/min using a spray pressure of 2.0 bars to form granules. The granulation is then dried in the fluidizing air of the column for about 10 minutes while maintaining the column at 30° C. The granulation is removed from the column and passed through a 20 mesh screen. Then 1.0 wt % of stearic acid lubricant is added to the granulation, with blending for 2 minutes, to produce the drug granulation.

Next, 700 ml of distilled water is added to a stainless steel mixing vessel and its mixer started, followed by adding 63 g of hydroxypropylcellulose to the water with mixing continued to produce a granulating solution. Then, 550 g of sodium carboxymethylcellulose, 290 g of sodium chloride, 77 g of hydroxypropylcellulose, and 20 g of ferric oxide are blended into a homogeneous blend and then passed through a 40 mesh screen. The just prepared blend is added to the granulator, and the granulating solution is sprayed onto the screened blend in a current of air warmed with an inlet air temperature of approximately 40° C. Next, the granulation is dried in the fluidizing air for about 10 minutes. Then, the granulation is removed from the column and passed through a 20 mesh screen. Next, 0.5 wt % of stearic acid pre-sieved through a number 80 mesh screen and 0.2 wt % of silicon dioxide also pre-sieved through a number 80 mesh screen is added to the granulation, and the ingredients are blended for 4 minutes.

Next, the first composition and the second composition are arranged into bilayer cores by compressing 125 mg of the first composition and 85 mg of the second composition together under a force of about 2 tons. The bilayer cores were coated with a coating solution comprising a binary solvent methylene chloride and methanol comprising cellulose triacetate and polyethylene glycol. The bilayers were coated in an Aeromatic ® coater with 500 g of coating composition until a uniform semipermeable coat is applied around the bilayers. The coated devices are dried in an air oven at 50° C. for 18 hours. Finally a 30 mil orifice exit is drilled through the semipermeable wall connecting the first composition with the exterior of the delivery device.

EXAMPLE 2

An osmotic device is manufactured as follows: first, a drug composition is prepared by adding 5 wt % to deprenyl hydrochloride, 25 wt % hydroxypropylmethylcellulose, 30 wt % hydroxypropylcellulose, 35 wt % polyvinyl pyrrolidone and 4.5 wt % lactic acid to a blender and the ingredients mixed for about 10 minutes. Then, while the ingredients are mixing, 60 ml of denatured, anhydrous ethanol is added slowly to the blender and the mixing continued for an additional five minutes. The wet granulation is passed through a 20 mesh screen, dried at room temperature for 16 hours and passed again through the 20 mesh screen. Finally, 0.5 wt % of magnesium stearate is added to the granulation and all the ingredients mixed in a roller mill for 1 to 3 minutes.

Next, the second composition is prepared by mixing 48 wt % sodium carboxymethylcellulose, 30 wt % of sorbitol, 20 wt % of hydroxypropylcellulose and 1 wt % ferric oxide, and the ingredients mixed in a blender to produce a homogeneous blend, which blend is passed through a 40 mesh screen. Next, 50 ml of denatured, anhydrous ethanol slowly is added to the blending mixture and all the ingredients mixed for an additional 5 minutes. The freshly prepared wet granulation is passed through a 20 mesh screen, allowed to dry at room temperature for 16 hours, and again passed through a 20 mesh screen. The screened granulation is mixed with 1 g of stearic acid in a roller mill for 1 minute.

Then, a two-layered press is used for forming a bilaminated drug core. First, the first composition comprising the anti-Parkinson deprenyl drug is added to the press and tamped, then, the second osmopolymer, osmagent composition is added to the press, and the two laminate pressed under a pressure of 1.8 tons into a contacting laminated arrangement.

Next, the laminate is surrounded with a semipermeable wall. The wall forming composition comprises 97 wt % cellulose acetate having an acetyl content of 39.8% and 3 wt % polyethylene glycol having a molecular weight of 400. The wall forming composition is dissolved in acetone-water (90:10 wt:wt) cosolvent to make a 4% solids solution. The wall forming composition is sprayed onto and around the bilaminate in an Wurster ® Air Suspension Coater.

Finally, the wall coated bilaminates are dried for 24 hours at room temperature. Then a 25 mil (0.635 mm) exit orifice is laser drilled on the drug laminate side of the osmotic device. The residual solvent is removed by drying the osmotic device for 48 hours at 50° C. and 50% relative humidity. The osmotic devices are then dried for 1 hour at 50° C. to remove excess moisture.

EXAMPLE 3

An osmotic dosage form is manufactured as follows: first, an anti-Parkinson drug pair comprising bromocriptine and deprenyl is made by adding 1700 ml of anhydrous ethanol to a blender, to which is added 150 g of polyvinyl pyrrolidone having a 40,000 molecular weight and the stirring continued to produce a solution. Next, 50 g of bromocriptine mesylate and 60 g of deprenyl hydrochloride is added to the polyvinyl pyrrolidone solution and the mixing continued until all the ingredients comprising the first composition are blended with the solvent.

Next, 600 g of hydroxypropylcellulose having a molecular weight of 100,000, 5 g of citric acid, and 150 g of polyvinyl pyrrolidone are blended to provide a homogeneous composition that is screened through a 40 mesh screen. The screened composition is added to a granulator column heated to 40° C. Then, the composition comprising the bromocriptine, the eldepryl and the polyvinyl pyrrolidone is added to the column to produce a fluidized granulation. Next, the granulation is dried in the fluidizing air of the column for about 10 minutes while maintaining the column at 30° C. The granulation is removed from the column and screened through a 20 mesh screen. Next, 1.0 wt % of magnesium stearate is added to the granulation accompanied by 2 minutes of blending to yield the bidrug granulation.

Next, 700 ml of distilled water is added to a mixer, followed by 63 g of hydroxypropylcellulose having a 70,000 molecular weight with continual mixing to yield a solution. Then, 550 g of sodium carboxymethylcellulose, 150 g of sodium chloride, 140 g of mannitol, and 70 g of hydroxypropylcellulose having a 60,000 molecular weight, and optionally 20 g of ferric oxide are blended into a homogeneous blend, and then screened through a 40 mesh screen. The screened blend is added to the granulation solution in the granulator and it is sprayed onto the blend. Then, the granulation is dried in the fluidizing air for about 10 minutes, removed from the column and screened through a 20 mesh screen. Then, 0.1 wt % of magnesium stearate and 0.3 wt % of silicon dioxide are added to the granulation, the ingredients blended for 6 minutes and screened through an 80 mesh screen to yield the expandable composition.

The first composition, and the second composition are arranged and pressed into bilayer cores by compressing 155 mg of the first composition and 95 mg of the second composition together under a force of 1.8 tons. The bilayers are coated with a coating solution comprising methylene chloride, methanol, cellulose triacetate, and polyethylene glycol. The bilayers are coated in an air suspension coater with 500 g of coating composition. The coated devices are dried in an air oven for 18 hours at 50° C. A 30 mil orifice is drilled through the semipermeable wall for connecting the drug composition with the exterior of the device.

EXAMPLE 4

A novel dosage form provided by the invention is manufactured as follows: first, 70% of mannitol is put through a 40 mesh screen and then sieved through a 60 mesh screen (all the mannitol that went through the 60 mesh screen is used for preparing the dosage form). Next, 5% eldepryl hydrochloride and 10% carbidopa-levodopa, 5% microcrystalline cellulose, and 8% polyvinyl pyrrolidone independently are screened through a 40 mesh screen, and the screened ingredients mixed in a blender with the mannitol for about 20 minutes to produce a homogeneous blend. Next, 1% silicon dioxide is screened through an 80 mesh screen, and then 1% magnesium is screened through an 80 mesh screen. The screened silicon dioxide and the screened magnesium stearate are added to the blend comprising the mannitol, eldepryl, carbidopa-levodopa, microcrystalline cellulose, and the polyvinyl pyrrolidone and blended for 5 minutes.

Next, 80% of a copolymer of N-vinyl lactam and N-vinyl pyrrolidone, 13% sodium chloride, and 5% of hydroxypropylmethylcellulose are wet granulated using ethyl alcohol as the granulating fluid. The wet granulation is screened through a 16 mesh screen and dried on trays at 50° C. in an oven overnight. The dried granulation is screened through a 16 mesh screen. Then a mixed lubricant comprising 1% magnesium stearate and 1% stearic acid is screened through a 80 mesh screen and added to the dried granulation. Finally, all the ingredients are blended for 5 minutes to yield a homogeneous blend.

A dosage form comprising a first drug layer and hydrophilic layer is prepared in a Carver ® press using a 5/16 inch, standard concave die. First, 150 mg of the composition comprising the drug layer is placed in the die and tamped to compress the granulation. Then, the second-forming layer comprising 75 mg of the hydrophilic polymer is placed on top of the first layer and compressed with 2.5 tons of force.

The two-layered laminate is surrounded with a wall in an Aeromatic ® Coater. The wall-forming composition comprised 51 g of cellulose acetate having an acetyl content of 43.5%, 9 g of hydroxypropyl cellulose, and a cosolvent comprising 1,170 ml of methylene chloride and 490 ml of methanol. During the wall-forming process, 960 ml of wall-forming solution are used to apply a 12.3 mg wall on each two-layered dosage form. The dosage forms are dried in an oven overnight at 50° C. to yield a final dry wall of 10.4 mg per dosage form. A single 15 mil, (0.325 mm) passageway is drilled through the wall connecting the exterior of the dosage form with the first layer. The first layer is selected by visual examination. In an automatic laser drilling technique, the drug layer is selected by the photo examination apparatus of the laser. The dosage form delivery 98.6% of its drugs in 24 hours.

EXAMPLE 5

The procedure of example 1 is repeated with the manufacturing steps are previously described, except that sodium chloride is replaced by an osmotically effective solute selected from the group consisting of potassium chloride, magnesium chloride, d-mannitol and lactose monohydrate.

EXAMPLE 6

An exterior, quick-releasing lamina comprising the drug pair bromocriptine mesylate and deprenyl hydrochloride and at least one quick-releasing member selected from the group consisting of hydroxypropylcellulose and hydroxypropylmethylcellulose are added to a fluid bed granulator and the materials blended in a moving current of air. Then, a granulating fluid is sprayed onto the fluidizing powders until the powders are agglomerated. Next the fluidizing process is continued until the granulation is dry. The immediate release lamina is compressed or air sprayed around the external surface of the delivery device to yield an immediate release coat comprising the bromocriptine and the deprenyl.

EXAMPLES 7 TO 14

A series of compositions for use as the first composition in an osmotic delivery device are prepared comprising the following ingredients: procyclidine, eldepryl and a member selected from the group consisting of hydroxypropylcellulose and hydroxypropylmethylcellulose; trihexyphenidyl, eldepryl and a member selected from the group consisting of hydroxypropylcellulose and hydroxypropylmethylcellulose; amantadine, eldepryl and a member selected from the group consisting of hydroxypropylcellulose and hydroxypropylmethylcellulose; carbidopa/levodopa, eldepryl and a member selected from the group consisting of hydroxypropylcellulose and hydroxypropylmethylcellulose; bromocriptine, eldepryl nd a member selected from the group consisting of hydroxypropylcellulose and hydroxypropylmethylcellulose; carbidopa, eldepryl and a member selected from the group consisting of hydroxypropylcellulose and hydroxypropyl methylcellulose; and wherein the anti-Parkinson drugs in the anti-Parkinson composition, or when in the delivery device keep their chemical integrity substantially-free of decomposition in the presence of other ingredients in the composition or in the delivery device.

EXAMPLE 15

An osmotic dosage form was prepared by the invention comprising a first composition comprising 125 mg of (4.9 wt %) bromocriptine mesylate, 63.0 wt % hydroxypropylcellulose, 28.0 wt % polyvinyl pyrrolidone and 4.1 wt % maleic acid; 85 mg of a second composition comprising 55 wt % sodium carboxymethylcellulose, 29 wt % sodium chloride, 14 wt % hydroxypropylcellulose, and 2 wt % ferric oxide; and a semipermeable wall comprising 95 wt % cellulose acetate having a 39.8% acetyl content, and 5 wt % polyethylene glycol having a 3350 molecular weight. The dosage form comprised a 30 mil orifice, and had a mean release rate of 0.302 mg/hr for 11.1 hours. Accompanying drawing FIG. 5 depicts the release rate in mg/hr for this dosage form, and accompanying drawing FIG. 6 depicts the cumulative amount release over 24 hours.

EXAMPLE 16

An osmotic dosage form was prepared as specified in Example 15 except that the first composition comprised 600 mg of (16 wt %) levodopa, 4 wt % carbodopa, 53 wt % hydroxypropylcellulose, 26 wt % polyvinyl pyrrolidone, and 1 wt % stearic acid and the second composition comprised a weight of 400 mg.

DISCLOSURE OF METHOD OF PERFORMING THE INVENTION

An embodiment of the invention pertains to a method for delivering a beneficial anti-Parkinson drug at a controlled rate orally to a warm-blooded animal in need of anti-Parkinson therapy, which method comprises the steps of: (A) admitting into the warm-blooded animal a dosage form comprising: (1) a wall surrounding a compartment, the wall comprising at least in part a semipermeable polymeric composition permeable to the passage of fluid and substantially impermeable to the passage of an anti-Parkinson drug; (2) a layer in the compartment comprising a formulation comprising a dosage unit amount of an anti-Parkinson drug for performing a therapeutic program: (3) a layer in the compartment comprising an osmotic formulation for imbibing and absorbing fluid for pushing the anti-Parkinson formulation from the dosage form; and, (4) at least one passageway in the wall for releasing the anti-Parkinson drug; (B) imbibing fluid through the semipermeable part of the wall as a rate determined by the permeability of the semipermeable wall and the osmotic pressure gradient across the semipermeable wall causing the osmotic layer to expand and swell; and (C) delivering the beneficial anti-Parkinson drug from the dosage form through the exit passageway to the warm blooded animal over a prolonged period of time.

In summary, it will be appreciated that the present invention contributes to the art an unobvious dosage form that possesses practical utility, can administer an anti-Parkinsonian drug at a dose metered release rate per unit time. While the invention has been described and pointed out in detail with reference to operative embodiments thereof, it will be understood to those skilled in the art that various changes, modifications, substitutions and omissions can be made without departing from the spirit of the invention. It is intended, therefore, that the invention embraces those equivalents within the scope of the claims which follows.

We claim:

1. A dosage form for administering an anti-Parkinson drug to a patient, wherein the dosage form comprises:
   (a) a wall that surrounds a compartment;
   (b) a bilayer core in the compartment, the bilayer core comprising:
      (i) a composition comprising 0.10 mg to 750 mg of an anti-Parkinson drug and a pharmaceutically acceptable carrier for the anti-Parkinson drug, which composition in the presence of fluid that enters the bilayer core forms a dispensable anti-Parkinson therapeutic formulation;
      (ii) a composition comprising a member selected from the group consisting of an osmagent and an osmopolymer that is substantially free of an unfavorable effect on the anti-Parkinson drug, and which member in the presence of fluid that enters the compartment increases in dimensions and displaces the anti-Parkinson formulation from the dosage form; and
   (c) at least one exit passageway in the wall that connects the exterior with the interior of the dosage form for delivering the dispensable formulation to the patient; and wherein,
   (d) the dosage form is manufactured comprising granules of the anti-Parkinson drug, and free of wax.

2. The dosage form for administering the anti-Parkinson drug according to claim 1, wherein the anti-Parkinson drug is a member selected from the group consisting of bromocriptine and its therapeutically acceptable salts.

3. The dosage form for administering the anti-Parkinson drug according to claim 1, wherein the anti-Parkinson drug is a member selected from the group consisting of eldepryl and its therapeutically acceptable salts.

4. The dosage form for administering the anti-Parkinson drug according to claim 1, wherein the anti-Parkinson drug is a member selected from the group consisting of lisuride, pergolide, mesulergine, levodopa, carbidopa, levodopa-carbidopa, amantadine, trihexyphenidyl, benztropine, biperiden, ethopropazine, procyclidine, benztropine mesylate, trihexyphenidyl hydrochloride, procyclidine hydrochloride and biperiden hydrochloride.

5. The dosage form for administering the anti-Parkinson drug according to claim 1, wherein the anti-Parkinson drug is present in the bilayer core as an anti-Parkinson drug pair, said pair comprising (e) a member selected from the group consisting of bromocriptine, lisuride, pergolide, mesulergine, levodopa, carbidopa, levodopa-carbidopa, amantadine, deprenyl, trihexyphenidyl, benztropine, biperiden, ethopropazine, procyclidine, and a (a) different member selected from the group consisting of bromocriptine, lisuride, pergolide, mesulergine, levodopa, levodopa-carbidopa, amantadine, deprenyl, trihexyphenidyl, biperiden, ethopropazine, and procyclidine.

6. The dosage form for administering the anti-Parkinson drug according to claim 1, wherein granules of anti-Parkinson drug are replaced with powdered anti-Parkinson drug.

7. A dosage form for administering an anti-Parkinson drug to a patient, wherein the dosage form comprises:
   (a) a wall that surrounds a compartment;
   (b) a bilayer core in the compartment, the bilayer core comprising:
      (i) a first layer composition comprising 0.10 mg to 750 mg of an anti-Parkinson drug and a pharmaceutically acceptable carrier for the anti-Parkinson drug, said first composition, in the presence of fluid that enters the bilayer core, forms a dispensable anti-Parkinson therapeutic formulation;
      (ii) a second layer composition comprising a member selected from the group consisting of an osmagent and an osmopolymer that is substantially-free of applying an unfavorable effect on the anti-Parkinson drug, and which member, in the presence of fluid that enters the compartment, increases in dimensions and displaces the anti-Parkinson formulation from the dosage form;
   (c) an immediate dose of an anti-Parkinson drug on the exterior wall of the dosage form;
   (d) at least one exit passageway in the wall that connects the exterior with the interior of th dosage form for delivering the dispensable formulation to the patient; and wherein,
   (e) the dosage form is manufactured comprising the anti-Parkinson drug and the bilayer core is free of wax.

* * * * *

UNITED STATES PATENT AND TRADEMARK OFFICE
CERTIFICATE OF CORRECTION

PATENT NO. : 5,221,536
DATED : June 22, 1993
INVENTOR(S) : David E. Edgren, et. al.

It is certified that error appears in the above-indentified patent and that said Letters Patent is hereby corrected as shown below:

On the Title page, item [54] and col. 1, line 2 and 3, delete "THE MANAGEMENT OF ABNORMAL POSTURE, TREMOR AND INVOLUNTARY MOVEMENT" and insert after the word "FOR" --ANTI-PARKINSON THERAPY--.

Signed and Sealed this

Eleventh Day of January, 1994

Attest:

BRUCE LEHMAN

Attesting Officer

Commissioner of Patents and Trademarks